(12) United States Patent
Akizuki et al.

(10) Patent No.: US 7,625,407 B2
(45) Date of Patent: Dec. 1, 2009

(54) TIBIAL PROSTHESIS WITH ASYMMETRIC ARTICULAR SURFACES

(75) Inventors: Shaw Akizuki, Nagano (JP); Michael C. Phipps, Hoboken, NJ (US); Kevin P. Sichler, Springfield, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 118 days.

(21) Appl. No.: 11/349,048

(22) Filed: Feb. 7, 2006

(65) Prior Publication Data

US 2007/0185581 A1    Aug. 9, 2007

(51) Int. Cl.
*A61F 2/38* (2006.01)
(52) U.S. Cl. .................. 623/20.32; 623/20.28
(58) Field of Classification Search ............... 623/13.12, 623/20.3–20.34
See application file for complete search history.

(56) References Cited

U.S. PATENT DOCUMENTS

| 4,963,152 | A | | 10/1990 | Hofmann et al. | |
|---|---|---|---|---|---|
| 5,047,057 | A | * | 9/1991 | Lawes | 623/20.29 |
| 5,344,460 | A | | 9/1994 | Turanyi et al. | |
| 6,074,425 | A | * | 6/2000 | Pappas | 623/18.11 |
| 6,235,060 | B1 | * | 5/2001 | Kubein-Meesenburg et al. | 623/20.31 |
| 2004/1014333 | | * | 7/2004 | Axelson et al. | 623/20.21 |
| 2008/0161918 | A1 | * | 7/2008 | Fankhauser et al. | 623/14.12 |

FOREIGN PATENT DOCUMENTS

WO    WO 2004/058108 A1 * 7/2004

OTHER PUBLICATIONS

Finsbury Orthopaedics Ltd. Medial rotation knee. Electronic version, from www.finsbury.org/public html/products/mrk.html, 2004; 5 pages.
Wright Medical Technology, Inc. Knee—total replacement: Learn about Advance® medial pivot knee. Electronic version, from www.wmt.com/Patients/knee/advance_mpk.asp, 2005; 4 pages.
Wright Medical Technology, Inc. Advance® total knee system—double-high/medial-pivot knees, Apr. 2005, 12 pages.
Kessler, Oliver et al. In vivo kinematic analysis of the knee with a new approach, received Feb. 7, 2006, 1 page.

* cited by examiner

*Primary Examiner*—David H. Willse
(74) *Attorney, Agent, or Firm*—Arthur Jacob

(57) ABSTRACT

A tibial prosthesis has tibial articular surfaces including a medial articular surface in a medial compartment and a lateral articular surface in a lateral compartment. The medial articular surface follows a first arcuate track having a first radius of curvature and a first posterior segment extending along a posterior aspect of the medial compartment to a first superior-interior location. The lateral articular surface follows a second arcuate track having a second radius of curvature and a second posterior segment extending along a posterior aspect of the lateral compartment to a second superior-inferior location. The second posterior segment has a slope extending in an inferior direction along the posterior aspect of the lateral compartment such that the second superior-inferior location is spaced a predetermined distance in an inferior direction from the first superior-inferior location.

12 Claims, 3 Drawing Sheets

TIBIAL PROSTHESIS WITH ASYMMETRIC ARTICULAR SURFACES

The present invention relates generally to the replacement of a natural knee joint with a knee prosthesis and pertains, more specifically, to achieving better emulation of natural knee joint kinematics in a prosthetic knee.

During articulation of a natural knee joint, flexion between the tibia and the femur takes place about a transverse axis while, at the same time, some relative rotation between the tibia and the femur occurs about a longitudinal axis. Such flexion and rotation is necessary to carry out a normal gait cycle. Current knee prostheses provide a femoral component having condylar bearing surfaces designed to closely match a tibial bearing surface provided by a tibial bearing insert. In some conventional knee prostheses, the condyles of the femoral component incorporate a reduced bearing radius to accomplish flexion and rotation of the femoral component on the tibial component. The articular surfaces provided by the tibial bearing member of the tibial component usually are symmetrical about the anterior-posterior centerline of the bearing member. Thus, the articular surfaces along both the anterior and posterior aspect of the medial compartment of the tibial bearing are symmetrical with the articular surfaces along respective anterior and posterior aspects of the lateral compartment of the tibial bearing to accommodate internal and external rotation during flexion.

Kinematic analyses indicate that the natural knee exhibits greater anterior-posterior translation in the lateral compartment relative to anterior-posterior translation in the medial compartment of the knee during flexion and rotation. As a result, recently developed prosthetic knees allow for increased internal rotation by providing the tibial bearing with articular surfaces which are asymmetrical about the anterior-posterior centerline.

The present invention presents an improvement which provides a tibial prosthesis with particular asymmetric articular surfaces for enabling a knee prosthesis to mimic more closely the movements of the natural knee for smooth knee kinematics and, in particular, rotational movements of the knee. As such, the present invention attains several objects and advantages, some of which are summarized as follows: Provides a knee prosthesis which better emulates movements of the natural knee for smooth knee flexion and extension and, in particular, rotational movements of the knee; allows a recipient of a knee prosthesis to flex the knee easily and with less effort, while offering smooth prosthetic knee kinematics, especially in accommodating rotational movements; provides a recipient of a total knee replacement with greater comfort and increased confidence in accommodating to the replacement; enables a more accurate emulation of the natural knee, and especially in rotational movements of the knee, with a prosthetic knee having relatively few component parts, all of which are configured for simplified manufacture; provides an effective replacement for the natural knee, exhibiting exemplary performance over an extended service life.

The above objects and advantages, as well as further objects and advantages, are attained by the present invention which may be described briefly as providing, in a tibial prosthesis having tibial articular surfaces extending between an anterior edge of the tibial prosthesis and a posterior edge of the tibial prosthesis, the tibial articular surfaces including a medial articular surface in a medial compartment and a lateral articular surface in a lateral compartment, an improvement wherein: the medial articular surface follows a first arcuate track having a first radius of curvature and a first posterior segment extending along a posterior aspect of the medial compartment to a first point located adjacent the posterior edge of the tibial prosthesis at a first inferior-superior location; and the lateral articular surface follows a second arcuate track having a second radius of curvature and a second posterior segment extending along a posterior aspect of the lateral compartment to a second point located adjacent the posterior edge of the tibial prosthesis at a second superior-inferior location; the second posterior segment having a slope extending in an inferior direction along the posterior aspect of the lateral compartment such that the second superior-inferior location is spaced a predetermined distance in an inferior direction from the first superior-inferior location.

The invention will be understood more fully, while still further objects and advantages will become apparent, in the following detailed description of preferred embodiments of the invention illustrated in the accompanying drawing, in which.

Figure 1:
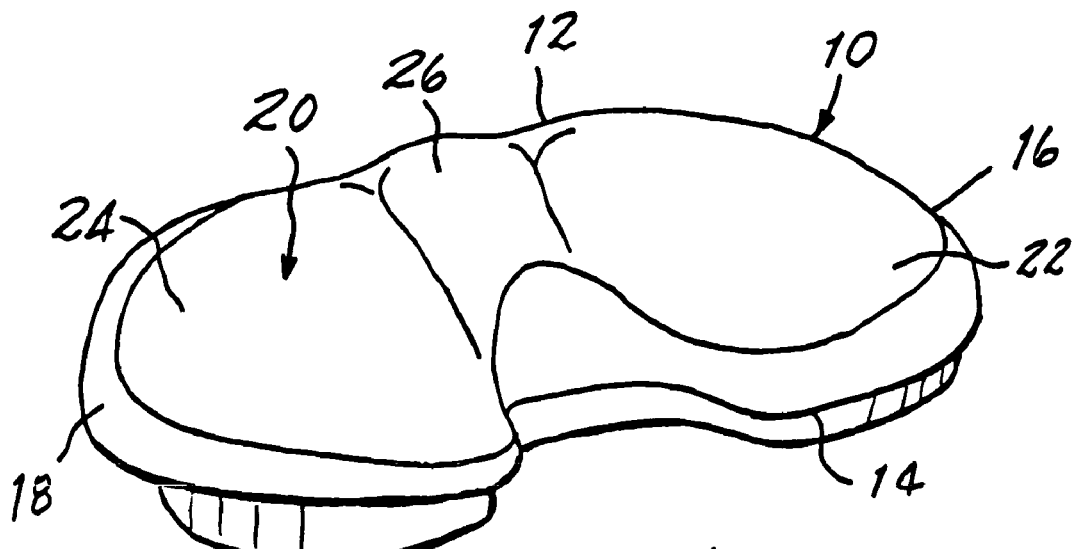
FIG. 1 is a lateral side, posterior edge and top pictorial view of the tibial bearing insert.
Figure 2:
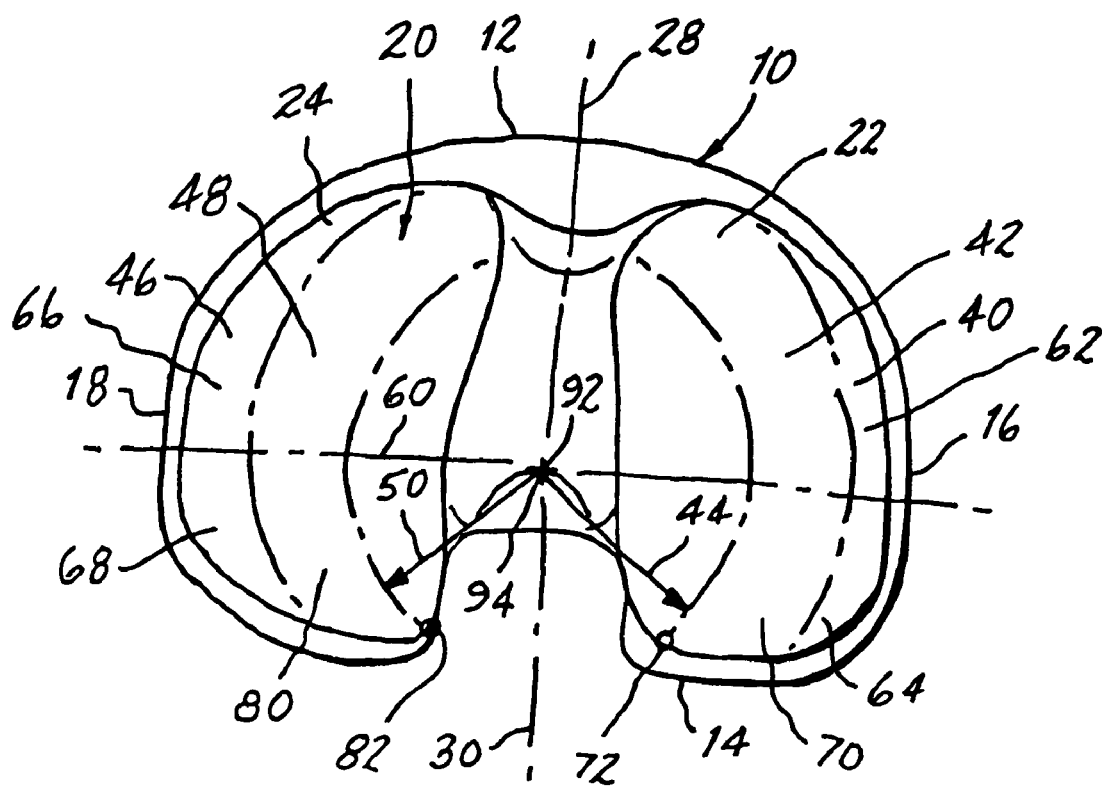
FIG. 2 is a top plan view of a tibial prosthesis in the form of a tibial bearing insert constructed in accordance with the present invention.

Referring now to the drawing, and especially to FIGS. 1 and 2 thereof, a tibial prosthesis constructed in accordance with the present invention is shown in the form of a tibial bearing insert 10 having an anterior edge 12, a posterior edge 14, a medial side 16 and a lateral side 18. A superior surface 20 includes three main compartments, namely, a medial compartment 22, a lateral compartment 24 and an eminence 26 located intermediate the medial compartment 22 and the lateral compartment 24, the eminence 26 extending along an anterior-posterior centerline 28 which lies in a sagittal plane 30. Tibial bearing insert 10 comprises a tibial bearing member for affixation to a tibial tray of a tibial component of a knee prosthesis, in a manner well known in the art.

The superior surface 20 includes a medial articular surface 40 which extends along a first arcuate track 42 within the medial compartment 22, and which has a first radius 44. A lateral articular surface 46 extends along a second arcuate track 48 within the lateral compartment 24 and has a second radius 50. The sulcus of the articular surfaces 40 and 46 lies in a coronal plane 60 which extends transversely across the tibial bearing insert 10, perpendicular to the sagittal plane 30, the coronal plane 60 dividing the medial articular surface 40 into an anterior aspect 62 and a posterior aspect 64, and dividing the lateral articular surface 46 into an anterior aspect 66 and a posterior aspect 68.

Figure 3:
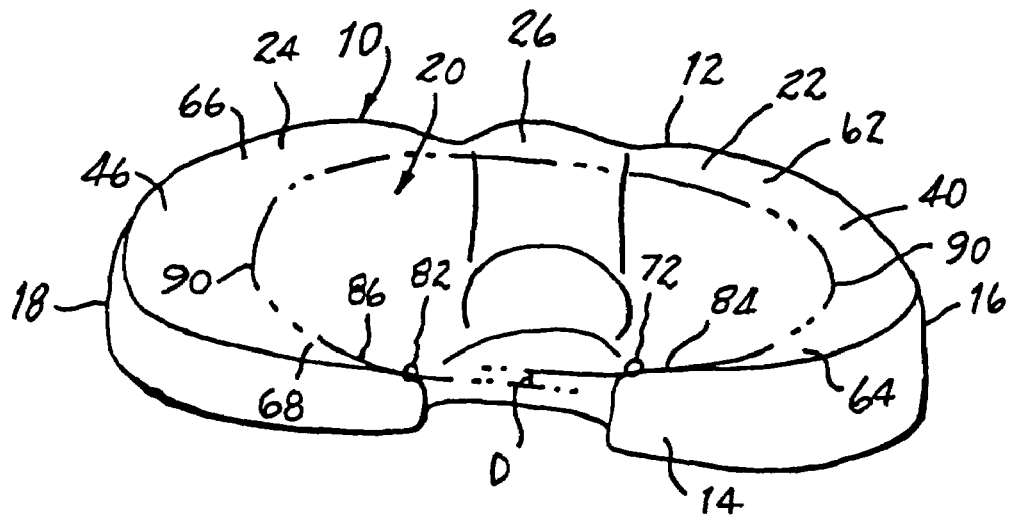
FIG. 3 is a posterior edge and top pictorial view of the tibial bearing insert.
Figure 4:
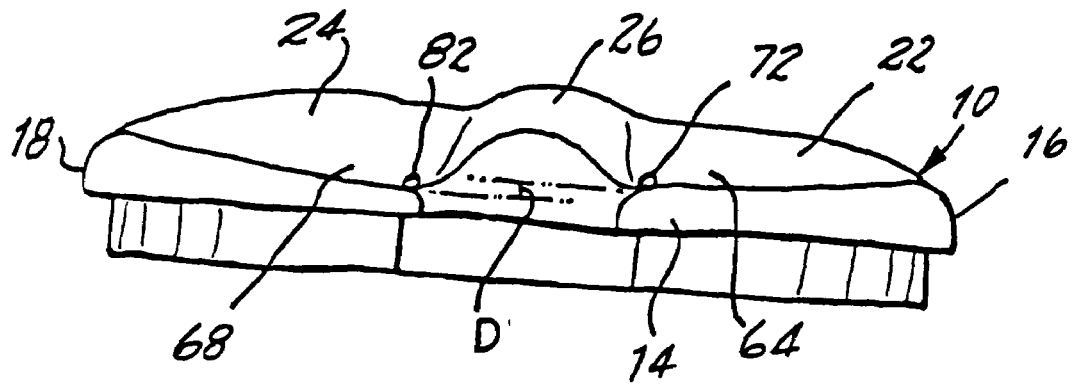
FIG. 4 is a posterior edge elevational view of the tibial bearing insert.
Figure 5:
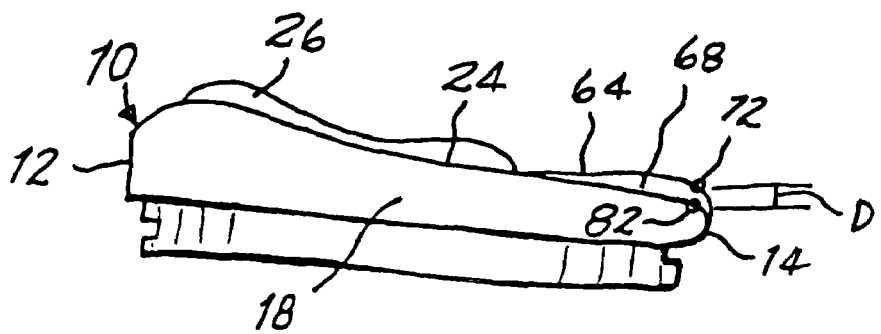
FIG. 5 is a side elevational view of the tibial bearing insert.

In order to allow for increased internal rotation and thereby accommodate the greater anterior-posterior translation in the lateral compartment relative to the anterior-posterior translation in the medial compartment exhibited in a natural knee during flexion and rotation, superior surface 20 is asymmetric in that the contour configuration of the posterior aspect 68 of the lateral articular surface 46 differs from the contour configuration of the posterior aspect 64 of the medial articular surface 40. With reference to FIGS. 3 through 5, as well as to FIGS. 1 and 2, the first arcuate track 42 includes a first posterior segment 70 which extends along the posterior aspect 64 of the medial articular surface 40 between the coronal plane 60 and a first point 72 located adjacent the posterior edge 14 at a first superior-inferior location. The second arcuate track 48 includes a second posterior segment 80 which extends along the posterior aspect 68 of the lateral articular surface 46 between the coronal plane 60 and a second point 82 located adjacent the posterior edge 14 at a second superior-inferior location. The second point 82 is spaced a prescribed distance D in an inferior direction relative to the superior-inferior location of the first point 72. In the preferred construction, the posterior segments 70 and 80 lie along corresponding segments 84 and 86 of an essentially helical path 90 having a pitch which establishes the distance D between the superior-inferior locations of the points 72 and 82. At the same time, in the most-preferred embodiment, the first and second radii 44 and 50 are maintained the same along the posterior segments 70 and 80 of the arcuate tracks 42 and 48 and extend from a common center 92 located on a longitudinal axis of rotation 94.

Figure 6:
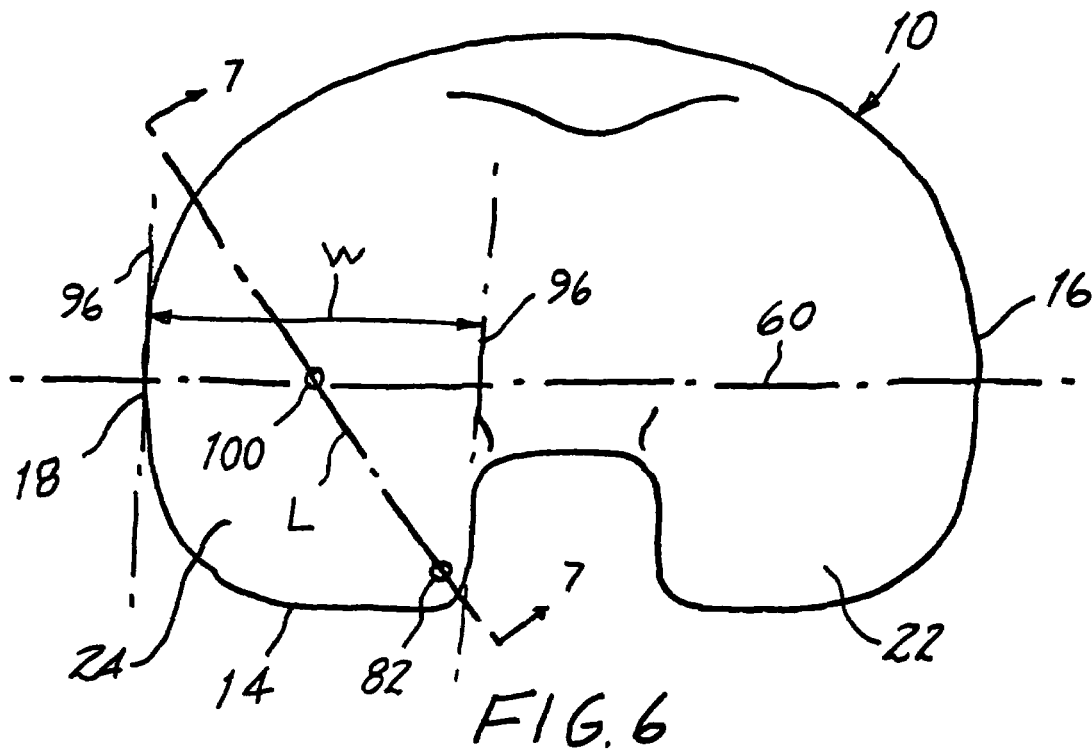
FIG. 6 is a somewhat diagrammatic top plan view of the tibial bearing insert.
Figure 7:
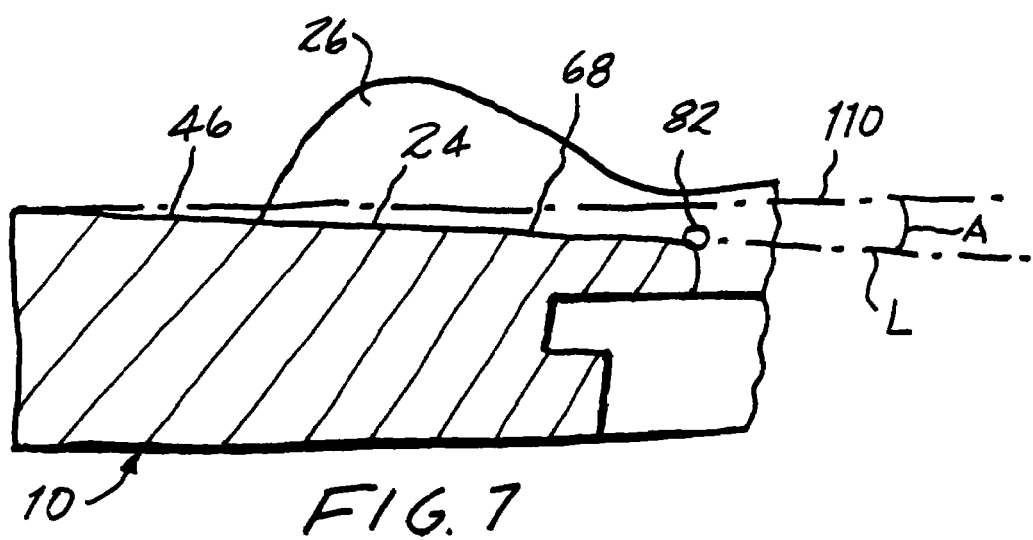
FIG. 7 is an enlarged, somewhat diagrammatic cross-sectional view taken along line 7-7 of FIG. 6.

Turning now to FIGS. 6 and 7, the distance D is established by the slope of the posterior segment 80 of the second track 48 from the coronal plane 60 to the second point 82. Lateral compartment 24 is seen to have a width W between laterally spaced apart boundaries 96 of the lateral compartment 24. Choosing a line L which extends between a centerpoint 100 located in the coronal plane 60 and, consequently, at the sulcus, midway between the boundaries 96 and second point 82, the slope of the posterior segment 80 is illustrated by an angle of declination A between the line L and an anterior-posterior plane 110 normal to the sagittal plane 30 and to the coronal plane 60 and passing through the centerpoint 100. In the preferred embodiment, the angle of inclination A is up to about 4°, with the most preferred angle of declination being about 2°.

It will be seen that the present invention attains the several objects and advantages summarized above, namely: Provides a knee prosthesis which better emulates movements of the natural knee for smooth knee flexion and extension and, in particular, rotational movements of the knee; allows a recipient of a knee prosthesis to flex the knee easily and with less effort, while offering smooth prosthetic knee kinematics, especially in accommodating rotational movements; provides a recipient of a total knee replacement with greater comfort and increased confidence in accommodating to the replacement; enables a more accurate emulation of the natural knee, and especially in rotational movements of the knee, with a prosthetic knee having relatively few component parts, all of which are configured for simplified manufacture; provides an effective replacement for the natural knee, exhibiting exemplary performance over an extended service life.

It is to be understood that the above detailed description of preferred embodiments of the invention is provided by way of example only. Various details of design and construction may be modified without departing from the true spirit and scope of the invention, as set forth in the appended claims.

The invention claimed is:

1. In a tibial prosthesis having tibial articular surfaces extending between an anterior edge of the tibial prosthesis and a posterior edge of the tibial prosthesis for enabling relative rotation between the tibial prosthesis and a femoral prosthesis engaged with the tibial prosthesis about a longitudinal axis of rotation during flexion of a prosthetic knee about a transverse axis, the tibial articular surfaces including a medial articular surface in a medial compartment and a lateral articular surface in a lateral compartment, an improvement wherein:

the medial articular surface follows a first arcuate track having a first radius of curvature extending from a corresponding center on a corresponding longitudinal axis and a first posterior segment extending along a posterior aspect of the medial compartment to a first point located adjacent the posterior edge of the tibial prosthesis and placed at a first inferior-superior location;

the lateral articular surface follows a second arcuate track having a second radius of curvature extending from a corresponding center on a corresponding longitudinal axis and a second posterior segment extending along a posterior aspect of the lateral compartment to a second point located adjacent the posterior edge of the tibial prosthesis and placed at a second superior-inferior location;

the second posterior segment follows a slope descending in an inferior direction relative to an anterior-posterior plane normal to a coronal plane and normal to a sagittal plane as the second posterior segment extends in a posterior direction along the posterior aspect of the lateral compartment such that the second superior-inferior location is placed at a predetermined distance in an inferior direction relative to the placement of the first superior-inferior location, thereby enabling the relative rotation between the tibial prosthesis and the femoral prosthesis along the first and second arcuate tracks to mimic corresponding kinematics of a natural knee; and the first posterior segment and the second posterior segment each extend along corresponding segments of a common helical path having a pitch for establishing the predetermined distance between the placement of the first and second superior-inferior locations.

2. The improvement of claim 1 wherein the first and second radii of curvature are maintained the same along the first and second posterior segments.

3. The improvement of claim 2 wherein the first and second radii extend from a common center.

4. The improvement of claim 3 wherein the common center is located on the longitudinal axis of rotation.

5. The improvement of claim 4 wherein:

the lateral compartment includes a lateral width between laterally spaced apart boundaries; the lateral articular surface includes a sulcus located in the coronal plane; and the slope is such that a line from a point located in the coronal plane and placed on the lateral articular surface midway between the laterally spaced apart boundaries makes a prescribed angle of declination with the anterior-posterior plane.

6. The improvement of claim 5 wherein the prescribed angle of declination is up to about 4°.

7. The improvement of claim 5 wherein the prescribed angle of declination is about 2°.

8. The improvement of claim 5 wherein the tibial prosthesis comprises a tibial bearing member for affixation to a tibial tray of a tibial component of a knee prosthesis.

9. The improvement of claim 1 wherein:

the lateral compartment includes a lateral width between laterally spaced apart boundaries;

the lateral articular surface includes a sulcus located in the coronal plane; and the slope is such that a line from a point located in the coronal plane and placed on the lateral articular surface midway between the laterally spaced apart boundaries makes a prescribed angle of declination with the anterior-posterior plane.

10. The improvement of claim 9 wherein the prescribed angle of declination is up to about 4°.

11. The improvement of claim 9 wherein the prescribed angle of declination is about 2°.

12. The improvement of claim 1 wherein the tibial prosthesis comprises a tibial bearing member for affixation to a tibial tray of a tibial component of a knee prosthesis.

* * * * *